(12) United States Patent
Gilfeather et al.

(10) Patent No.: US 6,635,839 B1
(45) Date of Patent: Oct. 21, 2003

(54) SEMICONDUCTOR ANALYSIS ARRANGEMENT AND METHOD THEREFOR

(75) Inventors: Glen P. Gilfeather, Del Valle, TX (US); Srikar V. Chunduri, Austin, TX (US); Brennan V. Davis, Austin, TX (US); David H. Eppes, Austin, TX (US); Victoria Bruce, Austin, TX (US); Michael Bruce, Austin, TX (US); Rosalinda M. Ring, Austin, TX (US); Daniel Stone, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/838,672

(22) Filed: Apr. 19, 2001

Related U.S. Application Data

(60) Provisional application No. 60/198,365, filed on Apr. 19, 2000.

(51) Int. Cl.[7] .................................................. B07C 5/00
(52) U.S. Cl. ..................................................... 209/576
(58) Field of Search ........................... 438/14; 209/573, 209/576, 574; 364/578

(56) References Cited

U.S. PATENT DOCUMENTS 5,646,870 A * 7/1997 Krivokapic ................. 364/578
6,066,822 A * 5/2000 Nemoto ...................... 209/573

OTHER PUBLICATIONS

D Kahng, T.A. Shankoff, T.T. Sheng and S.E. Haszko; "A Method for Area Saving Palnar Isolation Oxides Using Oxidation Protected Sidewalls", Nov. 1980, J Electrochem. Soc.: Solid State Sceince and Technology; p. 2468–2471.*

* cited by examiner

*Primary Examiner*—John F. Niebling
*Assistant Examiner*—Andre' C Stevenson

(57) ABSTRACT

Semiconductor die analysis is enhanced using a system that is adapted to perturb a die in a test chamber and to detect a response from the die to the perturbation. According to an example embodiment of the present invention, a semiconductor die analysis system includes a test chamber and a docking arrangement adapted to dock with the test chamber. A die is held in the docking arrangement and is presented inside of the test chamber when the docking arrangement is docked with the chamber. Two or more perturbation devices are used to perturb the die, and controller is adapted to control the perturbation. A data acquisition arrangement receives data from the die in response to the perturbation, and the data is used for analyzing the die.

23 Claims, 3 Drawing Sheets

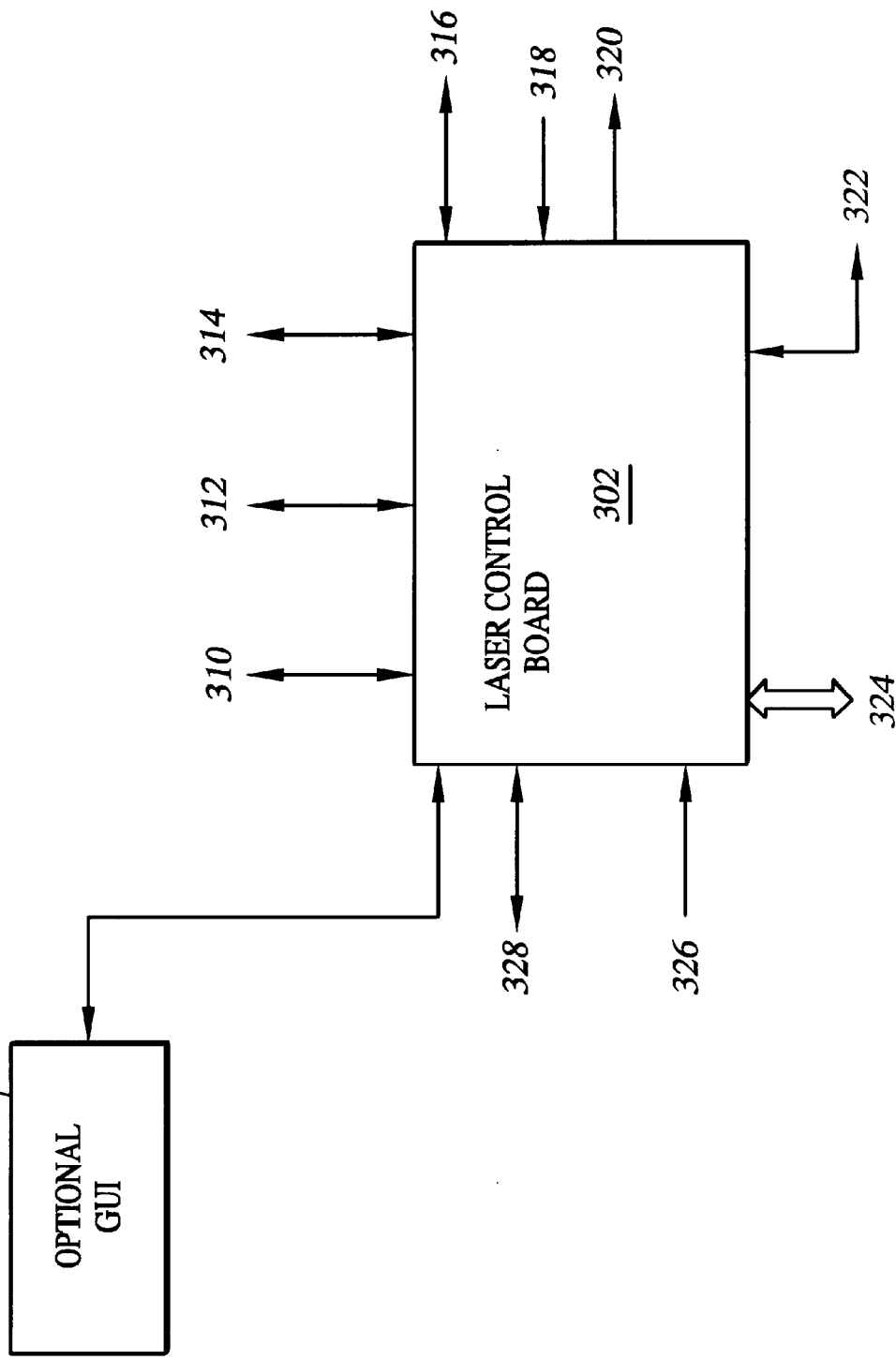

SEMICONDUCTOR ANALYSIS ARRANGEMENT AND METHOD THEREFOR

RELATED PATENT DOCUMENTS

This Application claims priority for common subject matter to U.S. Provisional patent application Ser. No. 60/198,365, filed on Apr. 19, 2000 and entitled "Semiconductor Analysis Arrangement and Method Therefore," which is fully incorporated herein by reference. The present application is related to co-pending documents identified by U.S. patent application Ser. No. 09/247,002, now U.S. Pat. No. 6,255,124, Jul. 3, 2001, Birdsley, and entitled "TEST ARRANGEMENT AND METHOD FOR THINNED FLIP CHIP IC", by U.S. patent application Ser. No. 09/166,833, Birdsley et al., filed on Oct. 5, 1998, entitled "ENDPOINT DETECTION FOR THINNING OF A FLIP CHIP BONDED INTEGRATED CIRCUIT" and also by U.S. patent application Ser. No. 09/409,217, filed on Sep. 30, 1999 and entitled "Defect Detection in Semiconductor Devices", which are assigned to the assignee of the present invention and incorporated herein by reference. This application is further related to U.S. patent application Ser. No. 09/838,717, entitled "Fiber Optic Semiconductor Analysis Arrangement and Method Therefore"; to U.S. patent application Ser. No. 09/838,671, entitled "Semiconductor Analysis Arrangement and Method Therefore"; and to U.S. patent application Ser. No. 09/838,667 now abandoned, entitled "Semiconductor Analysis Using Thermal Control," all of which are filed concurrently herewith.

FIELD OF THE INVENTION

The present invention relates generally to semiconductor device analysis and, more particularly, to devices and arrangements for enhancing the operability of semiconductor analysis.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the semiconductor packages which receive a die and on the exterior of the die, for connecting the packaged device to external systems, such as a printed circuit board.

As the manufacturing processes for semiconductor devices and integrated circuits increase in complexity, methods for testing and debugging these devices become increasingly important. Not only is it important to ensure that individual chips are functional, it is also important to ensure that batches of chips perform consistently. In addition, the ability to detect a defective manufacturing process early on is helpful for reducing the number of defective devices manufactured.

One type of semiconductor analysis involves conveniently directing perturbation signals, such as laser light, to a semiconductor device under test (DUT). When performing such analysis, however, many issues have to be managed. These issues include concerns such as laser leakage, calibration problems, and functional deficiencies. Further, a need exists for convenient approaches to presenting various types of perturbation signals to the DUT and managing the DUT's response intelligently and efficiently.

SUMMARY OF THE INVENTION

The present invention is directed to an approach for improving semiconductor analysis. The present invention is exemplified in a number of implementations and applications, some of which are summarized below.

The present invention is directed to addressing needs discussed above and is further useful in connection with the example embodiments disclosed in the above-referenced patent documents. According to an example embodiment of the present invention, a system is adapted for analyzing a semiconductor die using two or more perturbation devices adapted to perturb the die. The system includes a test chamber and a docking arrangement adapted to dock with the test chamber and to hold the semiconductor die for analysis in the test chamber. A controller is adapted to control the perturbation, and a response from the die to the perturbation is acquired using a data acquisition arrangement. The data is used, for example, to analyze the die and/or to control the analysis system, and can be accomplished in a test chamber using a variety of perturbation devices.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is a system for controlling a semiconductor analysis arrangement, according to another example embodiment of the present invention.

Figure 1:
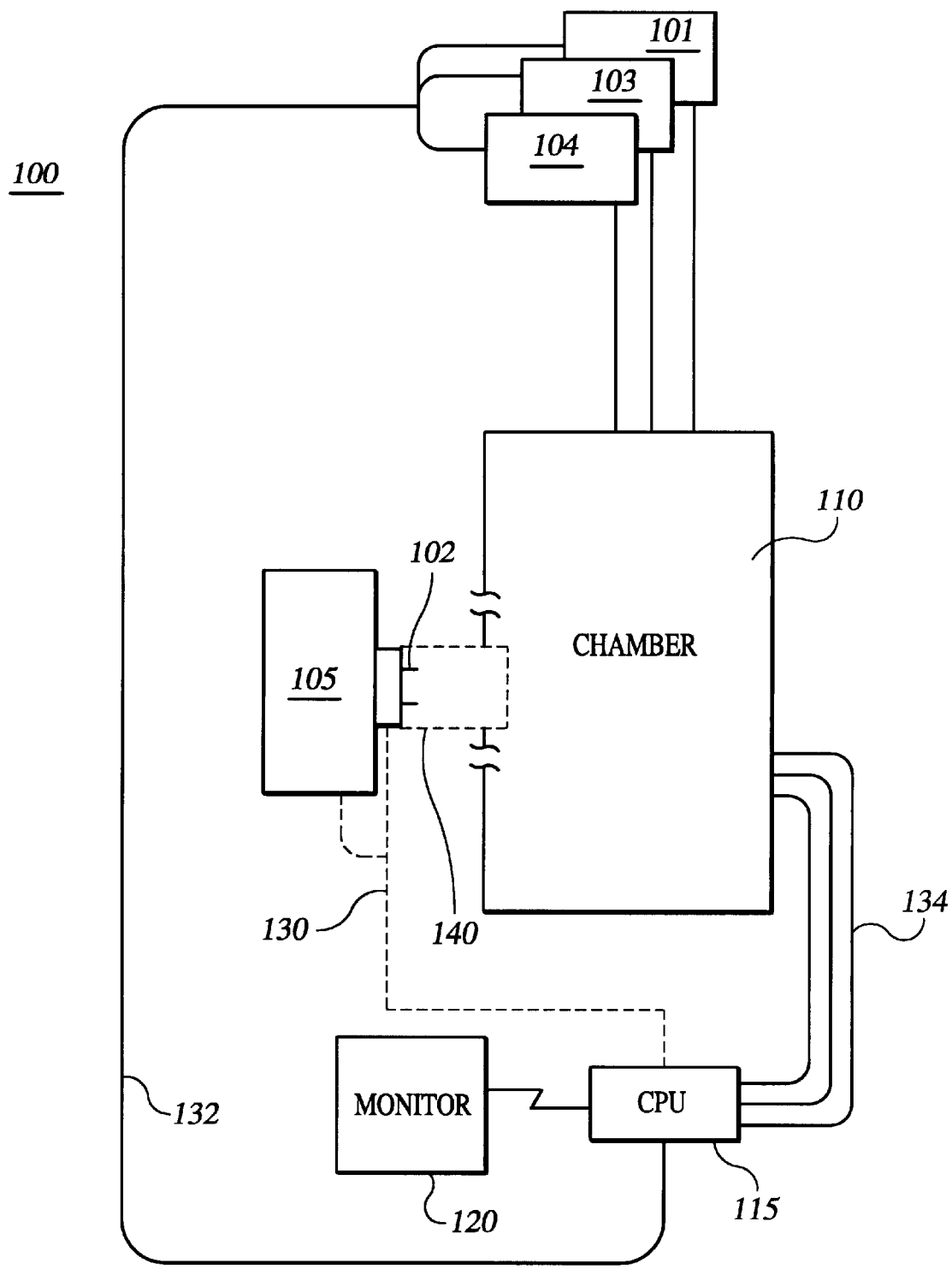
FIG. 1 is semiconductor analysis system, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of analysis, and the invention has been found particularly suited for semiconductor die analysis involving multiple tools and detectors. While the present invention is not necessarily limited to such devices, various aspects of the invention may be appreciated through a discussion of various examples using this context.

According to an example embodiment of the present invention, a semiconductor die analysis system is adapted to analyze a semiconductor die using two or more perturbation devices. The system includes a docking arrangement adapted to hold the die and to dock with a test chamber in a manner that presents the die inside of the test chamber. A controller is adapted to control the analysis system, such as for activating the perturbation devices and the docking arrangement. The perturbation devices are used to perturb the die, and a response of the die to the perturbation is detected using a data acquisition circuit adapted to receive the response. In this manner, the die can be tested using a variety of perturbation types, and a response from the die can be used for analysis.

FIG. 1 shows a system 100 for analyzing a semiconductor die 102, according to a more particular example embodiment of the present invention. The system includes a docking arrangement 105 adapted to hold the die 102 and to dock with a chamber 110 via a coupling arrangement 140. Various seals, gaskets, locking devices and other implements are adaptable for use in connection with the docking arrangement to dock with and seal the chamber to the docking arrangement. Once the docking arrangement is docked with the chamber, a plurality of perturbation devices 101, 103 and 104 are used to analyze the die. The perturbation devices may include, for example, an FIB device, a signal generator, a laser, an electron beam and/or an ion beam device. Operation data, such as chamber condition, die response, and other data, is provided to a central processing unit (CPU) 115. The CPU is coupled to the docking arrangement and adapted to receive response data from the die, such as electrical data obtained from die outputs, light reflections and emissions from the die. In one particular implementation, the perturbation devices 101, 103 and 104 are coupled to the CPU 115, and the CPU is adapted to control and receive feedback from the devices 101. A monitor 120 is coupled to the CPU 115 and adapted to display information such as response data and control data. In one particular implementation, the monitor is used as part of a graphical user interface (GUI) for controlling the system 100.

The perturbation devices can be used individually or in conjunction with each other for die analysis. In one implementation, each device is used to stimulate the die under a selected operating condition, and the response thereto is detected and noted for comparison to a response from a reference die. In addition, combinations of stimulation can be used to detect a response to the combination and similarly compared to a response from a reference die. In one instance, a signal generator and voltage supply are used to operate the die, one or more of the other perturbation devices is used to perturb the die, and a response from the die is detected. In this manner, various types of analysis, such as those employing light induced voltage alteration (LIVA), thermal induced voltage alteration (TIVA), optical beam induced current (OBIC) and critical timing path (CTP) methods can be performed in a single test arrangement.

For more information regarding example types of analysis that can be performed in connection with the present invention, reference may be made to U.S. Pat. No. 5,430,305, filed on Apr. 8, 1994 and entitled "Light-induced Voltage Alteration for Integrated Circuit Analysis:" to U.S. Pat. No. 5,523,694, filed on Jun. 4, 1996 and entitled "integrated Circuit Failure Analysis by Low-energy Charge-induced Voltage Alteration;" to U.S. Pat. No. 5,844,416, filed on Nov. 2, 1995 and entitled "Ion-beam Apparatus and Method for Analyzing and Controlling Integrated Circuits;" to U.S. patent application Ser. No. 09/259,542, now U.S. Pat. No. 6,177,989, Jan. 23, 2001, and entitled "Laser Induced Current for Semiconductor Defect Detection;" and to U.S. patent application Ser. No. 09/385,775, filed on Aug. 30, 1999 and entitled "Laser-excited Detection of Defective Semiconductor Device," which are fully incorporated herein by reference.

Figure 2:
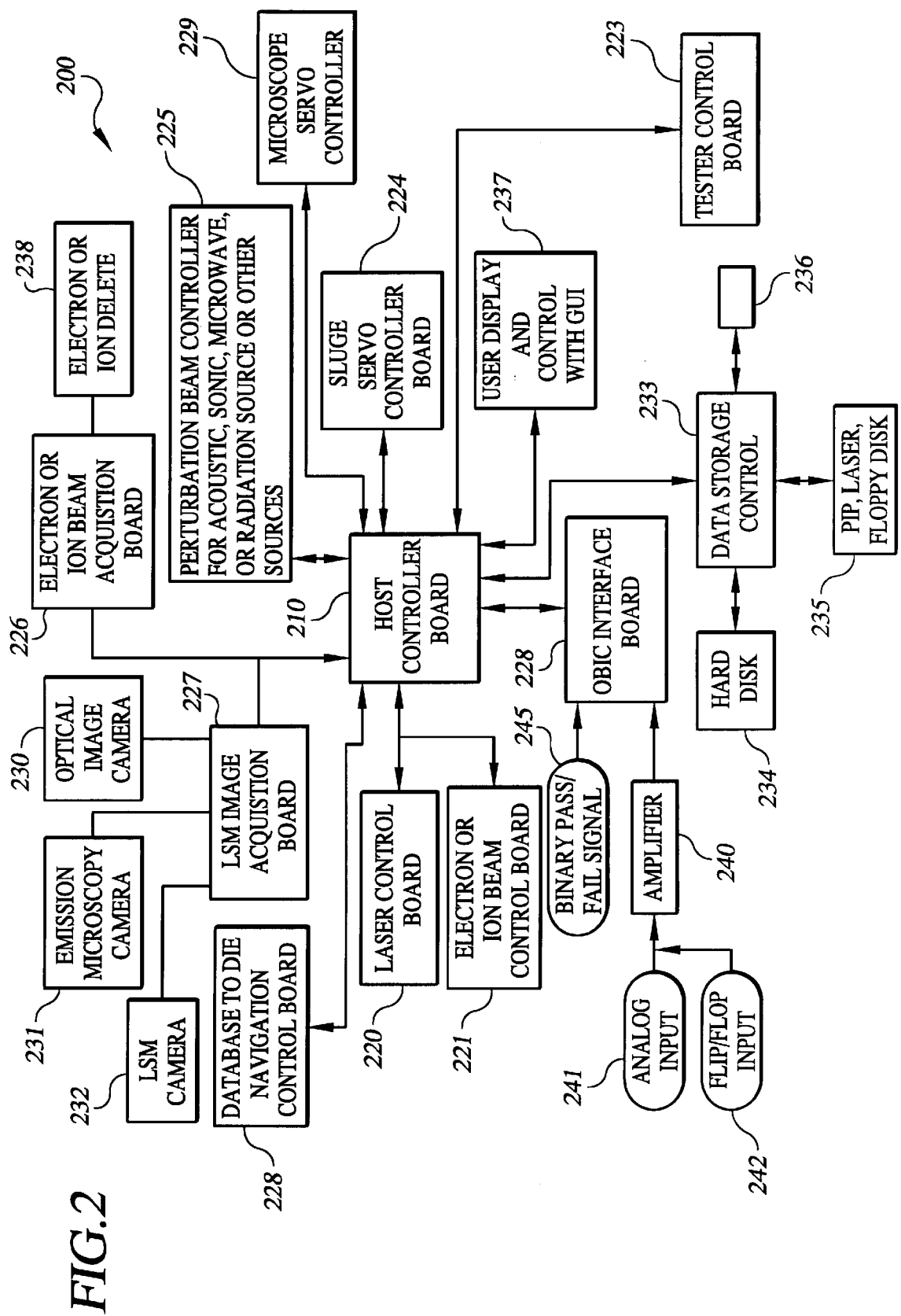
FIG. 2 is a system for analyzing a semiconductor die, according to another example embodiment of the present invention.

FIG. 2 is a schematic representation of a system 200 adapted to control and effect analysis of a semiconductor die, according to another example embodiment of the present invention. The system 200 may, for example, be used in connection with the controller discussed hereinabove. Various types of analysis methods, such as those employing optical beam, ion beam and electron beam analyses, are controllable using this system. The system includes a host controller board 210 coupled to a plurality of individual circuits, modules, control boards, perturbation devices, detection devices and other system control devices. In one implementation, the host controller board is coupled to a user interface, such as a computer or a display, and adapted to provide an indication of the response of the die to a user via the interface. For instance, the response may be displayed at the user interface as a graph showing a relative response of the die to a selected perturbation. For more information regarding various analysis techniques and systems applicable for use in connection with the system 200, reference may be made to U.S. patent application Ser. No. 09/409,217, filed on Sep. 30, 1999 and entitled "Defect Detection in Semiconductor Devices," which is fully incorporated herein by reference.

The perturbation device controllers include a laser control board 220 adapted to provide control signals to a laser perturbation device; an electron and/or ion beam control board 221 adapted to control one or both of an electron and ion beam perturbation device; and a perturbation beam controller 225 coupled to the host controller board 210 and adapted for one or more of acoustic, sonic, microwave and/or radiation perturbation sources. In addition, the system 200 is adaptable to couple to additional perturbation devices, such as an ion beam, electron beam, light and heat devices.

The system 200 includes a variety of detection devices and controllers, one or more of which may, for example, be used with the data acquisition circuit discussed above. The detection devices include an optical beam induced current (OBIC) interface board 222 adapted for interfacing with an arrangement that optically induces current in the die, and includes a binary pass/fail signal input 245 and an amplifier 240 adapted to amplify analog and flip/flop inputs 241 and 242. The amplified input is provided to the OBIC interface board 222 and may, for example, include an analog response from the die synchronized with the scan of a laser used to stimulate the die via the flip/flop input. In addition, the binary pass/fail input 245 optionally includes a signal representing a pass or fail state of a die being tested.

The detection devices also include an electron and/or ion beam acquisition board 226 coupled to an electron and/or ion detector 238. The detector 238 detects electrons and/or ions used in the analysis of the die (e.g., from an electron or ion source and/or from the die). The acquisition board 226 uses an output from the detector 238 to acquire a response and supplies that response to the host controller board 210.

Another detection device includes a microscope servo controller 229 adapted to control the position of a microscope used to image the die via a servo motor. Laser scanning microscope (LSM) camera 232, emission microscopy camera 231 and optical image camera 230 are adapted to image the die being analyzed. The cameras may include, for example, microscopes having servo position control via board 224. Image acquisition board 227 is coupled to cameras 232, 231 and 230 and acquires image data therefrom. The image data is provided to the host controller board 210 and used, for example, to position the die, position the analysis equipment, for detecting defects and other analysis applications.

The system 200 also includes a variety of other system control devices, including a data storage control device 233 coupled to a hard disk 234, an external disk 235 (e.g., a zip disk, a laser disk and/or a floppy disk), and a network device 236. The data storage control device is adapted to store a variety of data, including response data from the die and preset data for selected perturbation schemes (e.g., operating the die under selected conditions while perturbing the die with a laser using selected power, frequency and other parameters). In one particular implementation, the data storage control device is used to store and retrieve reference data for perturbing a reference die in a selected manner. The reference data is then used to compare a response from a die being analyzed to the reference die, and a condition of the die being tested is detected therefrom.

A tester control board 223 is also coupled to the host controller board and adapted to control a test chamber, such as chamber 110 in FIG. 1. Control of the test chamber may include, for example, coupling the docking arrangement 105 with the chamber 110 and initiating a vacuum pump to draw a vacuum on the chamber, power supply to the chamber and other applications. A stage servo controller board 224 is adapted to control a servo motor coupled to a stage adapted to hold the die. The servo motor is adapted to move the stage to position the die. In one implementation, the stage servo controller board 224 is adapted to position the die in response to one or more of the perturbation devices, detection devices and system control devices. In one implementation, the stage servo controller board is adapted to provide position feedback to the host controller board for identifying a position movement or relative position of the die.

In a more particular example embodiment of the present invention, a graphical user interface (GUI) and control board 237 are coupled to the host controller board and adapted to accept inputs from a user for controlling selected ones of the perturbation device controllers, detection device controllers and system controllers. Selections such as the type of analysis to be performed, analysis parameters and system control can be input via the GUI. In one particular implementation, the GUI is adapted to control the direction of a laser beam to a die using the laser control board 220 and the stage servo controller board 224.

FIG. 3 is a laser controller 300, according to a more particular example embodiment of the present invention. The laser controller may be used, for example, in connection with the systems and methods described herein, such as in connection with control board 220 in FIG. 2. The laser controller 300 includes a laser control board 302 having a plurality of input and output ports. The ports include laser energy control 310, laser beam selection 312, laser spot size control 314, laser pulse duty cycle control 316, mirror frequency and status input 318, mirror speed control 320, interlock 322, host controller interface 324, laser beam status 326 and filter position control 328. Each port is used to communicate signals for effecting the control and/or function related to its identification, such as for positioning laser and related equipment, for controlling the power and configuration of the laser and for ensuring interlocks are in place, such as a chamber door being closed. For example, when the interlock 322 receives a signal that is indicative of an interlock failing (e.g., a detected light leak or an unsealed vacuum), the laser energy control port 310 is used to turn the laser off, and a laser beam status 326 is used to verify that the beam is indeed off.

In a more particular example implementation, the laser controller 300 includes a graphical user interface (GUTI) 305. The GUI is adapted to make possible operator control of the laser controller 300, and in one implementation, is included as a part of GUI 237 of FIG. 2. The GUI 305 is adaptable for control of various analysis parameters, such as gas, temperature, cooling, beam focusing, signal latching, test configuration, monitor selections including contrast, brightness and color selection, scanning features, dwell time, scanning rate control, spot control, internal tool selection (e.g., with various analysis techniques, such as a dual-beam arrangement, photon beam analysis, TIVA, LIVA, OBIC, OBIRCH and CTP), and imaging controls such as overlays, labeling images and image processing.

While the present invention has been described with reference to several particular example embodiments, those skilled in the art will recognize that many changes may be made thereto without departing from the spirit and scope of the present invention, which is set forth in the following claims.

What is claimed is:

1. A semiconductor die analysis system comprising:
   a test chamber;
   a docking arrangement adapted to dock with the test chamber and hold a semiconductor die in the test chamber when docked therewith;
   a perturbation device adapted to perturb the die;
   a data acquisition arrangement adapted to acquire a response from the die to the perturbation; and
   a controller adapted to control the perturbation of the die.

2. The analysis system of claim 1, wherein the docking arrangement is adapted to form a vacuum seal with the test chamber, further comprising a vacuum arrangement adapted to draw a vacuum on the sealed test chamber.

3. The analysis system of claim 1, further comprising a plurality of detection arrangements adapted to detect a plurality of responses of the die to the perturbation devices and to send data representing the responses to the data acquisition arrangement.

4. The analysis system of claim 3, wherein the data acquisition arrangement is adapted to correlate the detected responses with at least one reference response and to detect a condition of the die in response to the correlation.

5. The analysis system of claim 4, wherein the data acquisition arrangement is adapted to identify a type of defect in the die as a function of the detected condition of the die.

6. The analysis system of claim 1, further comprising a graphic user interface (GUI) coupled to the data acquisition arrangement and adapted to receive user inputs and to provide the user inputs to the controller for controlling the analysis system.

7. The analysis system of claim 1, wherein the controller and the data acquisition arrangement are part of a circuit that includes a CPU.

8. A semiconductor die analysis system comprising:
   a test chamber;
   a docking arrangement adapted to dock with the test chamber and hold a semiconductor die in the test chamber when docked therewith;

a plurality of perturbation devices adapted to perturb the die and including a laser, a fiber optic cable adapted to direct light from the laser to the die, and at least one light detection arrangement adapted to detect a condition of light leakage from the cable and to generate a signal representing the detected leakage condition, wherein the controller is adapted to deactivate the laser in response to the detected leakage reaching a threshold level;

a data acquisition arrangement adapted to acquire a response from the die to the perturbation; and a controller adapted to control thee perturbation of the die.

9. A semiconductor die analysis system comprising:

a test chamber;

a docking arrangement adapted to dock with the test chamber and hold a semiconductor die in the test chamber when docked therewith;

a plurality of perturbation devices adapted to perturb the die;

a data acquisition arrangement adapted to acquire a response from the die to the perturbation; a controller adapted to control the perturbation of the die; and a coupling arrangement adapted to couple the docking arrangement to the test chamber.

10. The analysis system of claim 8, wherein the coupling arrangement includes a vacuum seal adapted to seal the docking arrangement to the test chamber.

11. The analysis system of claim 1, further comprising a host controller board coupled to the perturbation device and adapted to control the perturbation devices.

12. The analysis system of claim 11, wherein the perturbation devices include a laser having a laser control board, and wherein the laser control board is coupled to the host controller board, the host controller board being adapted to communicate control information to the laser control board for controlling the laser.

13. The analysis system of claim 12, wherein the laser control board is adapted to control at least one of laser aspects including laser energy control, laser beam type selection, laser spot size control, laser pulse duty cycle control, mirror frequency status, mirror speed control, and filter position control.

14. The analysis system of claim 12, wherein the laser control board has an interlock input coupled to an interlock, wherein the laser control board is adapted to deactivate the laser in response to receiving a signal at the interlock input.

15. A semiconductor die analysis system comprising:

a test chamber;

a docking arrangement adapted to dock with the test chamber and hold a semiconductor die in the test chamber when docked therewith;

a plurality of perturbation devices adapted to perturb the die;

a data acquisition arrangement adapted to acquire a response from the die to the perturbation;

a controller adapted to control the perturbation of the die; and wherein the perturbation devices include an elec tron beam device having a control board that is coupled to the host controller board, the host controller board being adapted to communicate control information to the control board for controlling the electron beam device.

16. A semiconductor die analysis system comprising:

a test chamber;

a docking arrangement adapted to dock with the test chamber and hold a semiconductor die in the test chamber when docked therewith;

a plurality of perturbation devices adapted to perturb the die, wherein the perturbation devices include an ion beam device having a control board, and wherein the control board is coupled to the host controller board, the host controller board being adapted to communicate control information to the control board for controlling the ion beam device;

a data acquisition arrangement adapted to acquire a response from the die to the perturbation;

a controller adapted to control the perturbation of the die; and a host controller board coupled to each of the plurality of perturbation devices and adapted to control the perturbation devices.

17. The analysis system of claim 11, wherein the host controller board is coupled to the data acquisition arrangement and adapted to receive data representing a response of the die and to provide an indication of the response to a user via a user interface.

18. A semiconductor die analysis system comprising:

a test chamber;

a docking arrangement adapted to dock with the test chamber and hold a semiconductor die in the test chamber when docked therewith;

a plurality of perturbation devices adapted to perturb the die;

a data acquisition arrangement adapted to acquire a response from the die to the perturbation and adapted to include at least one of: a laser scanning microscope (LSM), emission microscopy camera, optical image camera, OBIC defection arrangement, ion detector and an electron detector;

a controller adapted to control the perturbation of the die; and a host controller board coupled to each of the plurality of perturbation devices and to the data acquisition arrangement, and wherein the host controller board is adapted to control the perturbation devices and to receive data representing a response of the die and to provide an indication of the response to a user via a user interface.

19. The analysis system of claim 11, wherein the host controller board is coupled to a data storage arrangement adapted to store data from the host controller board and to retrieve data for use by the host controller board.

20. The analysis system of claim 11, wherein the docking arrangement includes a stage adapted to hold the die and a servo motor adapted to position the stage, wherein the host controller board is coupled to the servo motor and adapted to control the servo motor to position the die.

21. The analysis system of claim 11, wherein the data acquisition arrangement includes a microscope having a servo motor adapted to position the microscope, and wherein the host controller board is adapted to control the servo motor to position the microscope.

22. A semiconductor die analysis system comprising:

chamber means for testing a semiconductor die;

means for docking with the chamber means and for holding the semiconductor die in the chamber means when docked therewith;

means for perturbing the die;

means for acquiring a response to the perturbation from the die;

means for controlling the perturbation of the die; and means for positioning the die relative to at least one of: the data acquisition arrangement, and the means for perturbing the die.

23. A method for analyzing a semiconductor die, the method comprising:

providing a test chamber for testing a semiconductor die;

holding the semiconductor die in the test chamber with a docking arrangement adapted to dock with the test chamber;

perturbing the die with a perturbation device;

acquiring a response to the perturbation from the die; and controlling the perturbation of the die and positioning the die relative to at least one of: a reference point for the data acquisition, and the perturbation device.

* * * * *

UNITED STATES PATENT AND TRADEMARK OFFICE
CERTIFICATE OF CORRECTION

PATENT NO.    : 6,635,839 B1
DATED         : October 21, 2003
INVENTOR(S)   : Gilfeather et al.

It is certified that error appears in the above-identified patent and that said Letters Patent is hereby corrected as shown below:

<u>Title page,</u>
Item [56], OTHER PUBLICATIONS, "Sceince" should read -- Science --.

<u>Column 1,</u>
Lines 9, 25 and 27, "Therefore" should read -- Therefor --.

<u>Column 3,</u>
Line 60, "Analysis:" should read -- Analysis; --.
Line 62, "integrated" should read -- Integrated --.

<u>Column 7,</u>
Lines 1-13, should be indented as follows:
    a plurality of perturbation devices adapted to perturb the die and including a laser, a fiber optic cable adapted to direct light from the laser to the die, and a least one light detection arrangement adapted to detect a condition of light leakage from the cable and to generate a signal representing the detected leakage condition, wherein the controller is adapted to deactivate the laser in response to the detected leakage reaching a threshold level;
Line 16, "thee" should read -- the --.
Line 27, "a controller" should start a new paragraph.

<u>Column 7, line 67, and Column 8, line 1,</u>
"elec" and "tron" should read -- electron --.

<u>Column 8,</u>
Line 23, "a host..." should start a new paragraph.

Signed and Sealed this

Thirtieth Day of December, 2003

JAMES E. ROGAN
*Director of the United States Patent and Trademark Office*